United States Patent [19]

Reitz et al.

[11] 4,391,718
[45] Jul. 5, 1983

[54] SULPHONATED MONO-HYDRIC DIARYL PHENOL FORMALDEHYDE CONDENSATES, THEIR PREPARATION, THEIR USE AS DISPERSING AGENTS AND FORMULATIONS CONTAINING THEM

[75] Inventors: Gunther Reitz, Cologne; Karlhans Jakobs, Bergisch Gladbach; Günther Boehmke, Leverkusen, all of Fed. Rep. of Germany

[73] Assignee: Bayer Aktiengesellschaft, Leverkusen, Fed. Rep. of Germany

[21] Appl. No.: 292,867

[22] Filed: Aug. 14, 1981

[30] Foreign Application Priority Data

Sep. 4, 1980 [DE] Fed. Rep. of Germany ....... 3033329

[51] Int. Cl.$^3$ .................. B01F 17/30; C08G 8/18
[52] U.S. Cl. .................................. 252/8.7; 8/560; 8/589; 8/922; 252/351; 252/353; 252/354; 528/150; 528/171
[58] Field of Search ............... 8/560, 589; 252/354, 252/351, 353, 8.7; 528/150, 171, 560, 589

[56] References Cited

U.S. PATENT DOCUMENTS

| | | | |
|---|---|---|---|
| 3,872,056 | 3/1975 | Daubach et al. | 8/527 |
| 4,079,040 | 3/1978 | Ribka et al. | 528/150 |
| 4,101,489 | 7/1978 | Reitz et al. | 524/541 |
| 4,325,890 | 4/1982 | Reitz et al. | 8/589 |

FOREIGN PATENT DOCUMENTS

| | | |
|---|---|---|
| 701075 | 12/1940 | Fed. Rep. of Germany . |
| 1719417 | 5/1973 | Fed. Rep. of Germany . |
| 2934980 | 3/1981 | Fed. Rep. of Germany . |
| 246989 | 11/1947 | Switzerland . |
| 252305 | 10/1948 | Switzerland . |
| 615190 | 3/1949 | United Kingdom . |
| 1107226 | 3/1968 | United Kingdom . |

*Primary Examiner*—A. Lionel Clingman
*Attorney, Agent, or Firm*—Sprung, Horn, Kramer & Woods

[57] ABSTRACT

Reaction products which are prepared by sulphonation or sulphomethylation and formaldehyde condensation of compounds of the formula

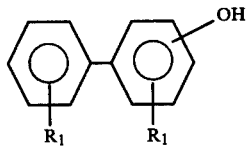

wherein
$R_1$ represents $C_{1-4}$-alkyl, and, if appropriate, subsequent conversion of the resulting sulphonic acids into their salts are used as dispersing agents.

1 Claim, No Drawings

SULPHONATED MONO-HYDRIC DIARYL PHENOL FORMALDEHYDE CONDENSATES, THEIR PREPARATION, THEIR USE AS DISPERSING AGENTS AND FORMULATIONS CONTAINING THEM

The invention relates to reaction products which are prepared by sulphonation or sulphomethylation and formaldehyde condensation of compounds of the general formula

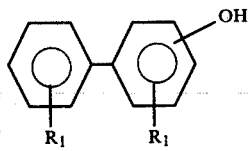
(I)

wherein
$R_1$ denotes $C_{1-4}$-alkyl, preferably $CH_3$,
and, if appropriate, subsequent conversion of the resulting sulphonic acids into their salts.

Isomeric compounds of the formula (I) are described, for example, in "Beilsteins Handbuch der Organischen Chemie" ("Beilstein's Handbook of Organic Chemistry"), E III 6 (1967), pages 3406–3410. One preparation process, by which a large number of the isomers are formed, comprises reacting a chlorotoluene, for example o-chlorotoluene, with strong alkalis, for example sodium hydroxide solution, at high temperatures.

Compounds which are prepared by sulphonation and formaldehyde condensation of (I) are preferred, sulphonation being understood as reaction with chlorosulphonic acid, $SO_3$, oleum or $H_2SO_4$. The reaction with oleum is preferred, and the reaction with sulphuric acid is particularly preferred.

The sulphonation is carried out before the formaldehyde condensation. The structure of the products thereby formed has not been clarified completely. Compounds of the general formula

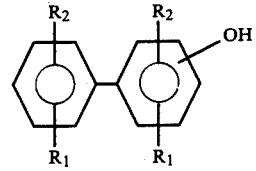
(II)

wherein
$R_2$ denotes H or $SO_3H$, and at least one $R_2$ is $SO_3H$, are probably formed.

There is also some evidence that other compounds are also formed, for example small amounts of the sulphone of (I) having the formula

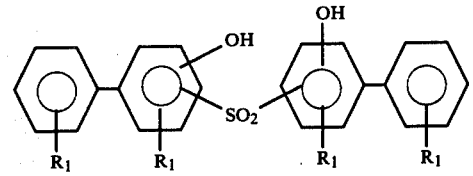
(III)

or products having a structure which has not yet been clarified.

Sulphomethylation gives compounds in which at least one of the aromatic rings of (I) is substituted by the radical $-CH_2-SO_3X$ wherein
X denotes H, a metal cation, that is to say Na, K, Ca/2 or Mg/2, or $N(R_3)_4$ and
$R_3$ denotes H or $C_{1-4}$-alkyl, which is optionally substituted by OH. Formaldehyde condensation of the sulphonated or sulphomethylated compounds (I) gives high-molecular compounds containing 2 to 100, preferably 2–20, units derived from the compounds (I). These units are chiefly linked with one another by methylene bridges originating from the formaldhyde.

One or both of the aromatic rings of (I) can carry methylene bridges. It is also conceivable that $-CH_2OH$ groups, which likewise originate from the formaldehyde, are bonded to individual aromatic rings, especially if these are terminal.

The invention also relates to processes for the preparation of the new compounds. These processes are characterised in that a water-soluble emulsifier is added before or during the formaldehyde condensation.

This emulsifier can be anionic, cationic or non-ionic. It is preferably anionic or non-ionic, and particularly preferably non-ionic. The anionic emulsifiers are, for example, alkyl-sulphonates or alkyl-benzenesulphonates with 10 to 25 C atoms in the alkyl radical. The non-ionic emulsifiers are, for example, reaction products of fatty acids, fatty acid amides, aliphatic alcohols or amines with in each case 10 to 22 C atoms, araliphatic alcohols or alkylphenols with in each case 1 to 20 C atoms in the aliphatic or alkyl groups, which have been reacted with 8 to 50 equivalents of ethylene oxide. Of the non-ionic emulsifiers, ethoxylated alcohols and ethoxylated alkylphenols are particularly preferred.

In detail, the process for the preparation of the products according to the invention is as follows:

The compounds (I) are reacted with a sulphonating agent, for example chlorosulphonic acid, $SO_3$, oleum or, particularly preferably, sulphuric acid, in a molar ratio of (I):sulphonating agent of 1:(0.9–2.5), preferably 1:(1.4–2). The reaction with $H_2SO_4$ is carried out at 80°–180° C., preferably 110°–160° C., in 0.5 to 10 hours, preferably 1–4 hours, the water of reaction being distilled off. During the reaction, a vacuum of less than 200 mm Hg, preferably less than 60 mm Hg, is advantageously applied. The degree of sulphonation, that is to say the number of $SO_3H$ groups bonded to one mol of the compounds (I), is 0.8–2.1, preferably 1.0–2.0, mols.

After the sulphonation, 0.25–15%, preferably 1–5%, relative to the weight of (I), of emulsifier and 0.4–4 mols, per mol of (I), of aqueous formaldehyde solution preferably with a content of 20–40%, and, if appropriate, water are added in any desired sequence.

In a preferred process, the emulsifier is mixed with the sulphonic acid melt and water is then added, if appropriate, followed by the formaldehyde solution. The reaction in this case is carried out with 0.4–4 mols of formaldehyde, preferably 0.6–2 mols of formaldehyde, per mol of (I) at 100°–180° C., preferably 120°–160° C., in the course of 1–10 hours, preferably 3–8 hours. The formaldehyde condensation can be carried out at an acid or alkaline pH value. A pH of 0–7 is preferred.

The sulphomethylated compounds according to the invention are preferably prepared from the compound (I), a sulphite, for example $Na_2SO_3$, $Na_2S_2O_5$ or $NaHSO_3$, and formaldehyde in a molar ratio of 1:(0.9–2):(2.4–3) in an alkaline medium at 100°–180° C., preferably 120°–160° C., in the course of 2–10 hours, preferably 4–8 hours. The sulphomethylated compounds can also be prepared by a stepwise process in which the compound (I) is first subjected to a precondensation reaction with 0.8–2.2 mols of formaldehyde at 60°–120° C. in the course of 5–120 minutes, preferably with 1.4–2.0 mols of formaldehyde at 80°–100° C. in the course of 10–60 minutes, to give the corresponding methylol compounds, the methylol compounds are then converted into the sulphomethyl compounds with 0.9–2.2 mols, preferably 1.4–1.9 mols, of bisulphite at 80°–180° C. in the course of 10–120 minutes, preferably at 100°–140° C. in the course of 30–90 minutes, and the sulphomethyl compounds are then converted into the high-molecular condensates according to the invention with 0.9–2.8 mols, preferably 1.0–1.5 mols, of formaldehyde in the course of 2–10 hours at 100°–180° C., preferably in the course of 4–10 hours at 120°–160° C. All the molar data are relative to 1 mol of (I).

In the one-stage synthesis, the emulsifier is added at the start with the other components. In the multi-stage synthesis, the emulsifier is preferably added after the preparation of the sulphomethyl compounds and before the formaldehyde condensation.

Brownish-coloured 20–40% strength solutions which can be dried to give friable powders which can easily be dissolved again in water are formed.

The compounds according to the invention are excellent dispersing agents, especially for organic dyestuffs and pigments. They can be used for the preparation of pulverulent or liquid dyestuff formulations, or as a dispersing agent in the dyebath.

A particular advantage of the compounds according to the invention is their levelling property in the dyeing of polyester with disperse dyestuffs, in particular in high-temperature dyeing.

The exceptionally good compatibility of the formaldehyde condensates according to the invention with non-ionic emulsifiers, in particular with ethoxylates of fatty acids, fatty alcohols, alkylphenols and fatty amines should also be mentioned. This compatibility means that such non-ionic emulsifiers are completely homogeneously miscible with the dispersing agents according to the invention as long as the degree of ethoxylation is sufficiently high, for example greater than 6 ethoxy groups.

In spite of their salt-like character, the compounds according to the invention are completely soluble in organic solvents, such as glycols or diglycols, triglycols and higher glycols, giving homogeneous solutions.

The condensates according to the invention are in the form of acids or, preferably, in a neutral form. To prepare the salts, the acids are neutralised by adding a base, preferably NaOH, before or after the formaldehyde condensation.

Auxiliary mixtures containing the components listed below are preferably used for dyeing polyester with disperse dyestuffs, especially under high-temperature conditions:

(1) aliphatic, araliphatic or alkylaromatic alcohols, carboxylic acids or carboxylic acid amides which have 12 to 22 C atoms and have been reacted with 3–8 mols of ethylene oxide per mol of starting compound, (2) aliphatic, araliphatic or alkylaromatic alcohols, carboxylic acids or carboxylic acid amides which have 12 to 22 C atoms and have been reacted with 9 or more mols of ethylene oxide per mol of starting compound, and (3) the condensates according to the invention.

Examples of component (1) which may be mentioned are ethoxylated fatty alcohols, fatty acids and fatty acid amides with 12–20 C atoms and ethoxylated alkylphenols with 4–16 C atoms in the alkyl group. Saturated and unsaturated fatty alcohols which have 14–18 C atoms and have been reacted with 4–7 mols of ethylene oxide per mol of starting compound are preferred.

Examples of component (2) are ethoxylated fatty alcohols, fatty acids and fatty acid amides with 12–20 C atoms and ethoxylated alkylphenols with 4–16 C atoms in the alkyl group. Alkylphenols which have 6–12 C atoms in the alkyl group and have been reacted with 9–20 mols of ethylene oxide per mol of starting compound are preferred.

The aliphatic groups in components (1) and (2) can be saturated or unsaturated.

In the case of component (3), those condensates which are formed by sulphonation and formaldehyde condensation of (I) are preferred.

Components (1), (2) and (3) are present, for example, in a mixing ratio of 1:(0.1–10):(0.1–40), preferably 1:(0.5–2):(0.2–1). The ratio of the sum of components (1) and (2) to component (3) is 1:(0.05–10), preferably 1:(0.1–1).

The three components are homogeneously miscible in a concentrated aqueous solution. According to experience, this solution has a solids content of up to 80%, preferably up to 70%.

Components (1), (2) and (3) are mixed by bringing together the pure components or their aqueous mixtures or solutions. Component (3) is preferably employed in aqueous solution, but components (1) and (2) are preferably employed in anhydrous form. After bringing the components together, they are mixed at temperatures up to 100° C., preferably at room temperature, whilst stirring. If the mixture is not clear, solvent is added, whereupon it becomes completely homogenous. Inorganic or organic compounds are suitable solvents. Organic compounds which may be mentioned are those in which the weight ratio of hydroxyl, amino and/or ether groups to the total molecule is high, that is to say methanol, ethanol, glycol, di-, tri- or tetra-ethylene glycol, polyglycol, the monomethyl and dimethyl ethers of the various glycols, glycerol, pentaerythritol, tri-methylolpropane, mono-, di- or tri-ethanolamine and propylene glycol and butylene glycol. Examples of amines which may be mentioned are 1,2- and 1,3-diamines and polyamines derived therefrom.

The compounds formed by etherification, ethoxylation and/or propoxylation of the compounds mentioned are likewise suitable. Of the organic compounds, glycol is preferred, and water is the preferred inorganic compound. It is particularly preferable to use water as the solvent.

The auxiliary mixture of components (1), (2) and (3), called auxiliary for short in the text which follows, is an outstanding levelling agent for use in the dyeing of synthetic fibres, in particular synthetic polyester fibres, with organic disperse dyestuffs. Dyeing is preferably carried out under high temperature conditions, that is to say in closed dyeing apparatuses at temperatures above 100° C.

The auxiliary is added to the dye liquor in amounts of 0.5–4 g/l of dye liquor, preferably 1–2 g/l of dye liquor, the amount in g relating to the solids content in the auxiliary.

EXAMPLE 1

100 g of a hydroxyditolyl isomer mixture (compound (I), $R_1=CH_3$, prepared from chlorotoluene,) and 80 g of sulphuric acid are heated to 150° C. under a waterpump vacuum for 3 hours, during which about 15 g of $H_2O$ are distilled off. 2 g of a nonylphenol which has been reacted with 10 mols of ethylene oxide are added and the reaction mixture is mixed until homogeneous.

300 ml of $H_2O$ are then added dropwise and 45% strength sodium hydroxide solution are added, using a pH meter, until the pH value reaches 6. 50 g of 30% strength aqueous formaldehyde solution are then added and the mixture is heated to 145° C. for 6 hours. $\lambda_{max}=207$ nm (in water).

EXAMPLE 2

100 g of a hydroxyditolyl isomer mixture (compound (I), $R_1=CH_3$) and 100 g of sulphuric acid are heated to 140° C. under a waterpump vacuum for three hours, during which about 18 g of $H_2O$ are distilled off. 3 g of an oleyl alcohol which has been reacted with 20 mols of ethylene oxide are added, and the components are mixed until a homogeneous reaction mixture is obtained. 300 ml of $H_2O$ are then added dropwise, and the mixture is neutralised with 45% strength sodium hydroxide solution, using a pH meter, until the pH value reaches 6. 80 g of 30% strength aqueous formaldehyde solution are then added and the mixture is heated to 145° C. for 6 hours.

EXAMPLE 3

A cheese weighing 500 g is immersed, in a liquor ratio of 1:15, in a solution which contains, per liter, 0.48 g of oleic acid ethoxylated with 6 mols of ethylene oxide, 0.48 g of nonylphenol which has been ethoxylated with 10 mols of ethylene oxide and 0.75 g of the product solution prepared according to Example 1. The alternately circulating liquor is warmed to 75° C. and, after the addition of 2 g/l of monosodium phosphate, is adjusted to a pH of 4.5–5 with acetic acid. The following dyestuffs are then added in dispersed form (the weight data are based on the pure dyestuff): 0.3 g of Disperse Yellow 64 (C.I. No. 47023), 0.25 g of Disperse Red 65 (C.I. No. 11228) and 0.36 g of Disperse Blue 56 (C.I. No. 63285). The liquor is warmed in the course of 45–60 minutes to 130° C. and dyeing is carried out at this temperature for 60 minutes. The liquor is then cooled and the cheese is rinsed and dried.

The cheese is dyed a neutral grey shade and is distinguished by an excellent ending.

EXAMPLE 4

The procedure followed is as in Example 3, but the dye liquor contains, per liter, not 0.75 g of the solution prepared according to Example 1 but 0.75 g of the product solution prepared according to Example 2.

In this case also, the dyed cheese is distinguished by an excellent ending.

EXAMPLE 5

Product A = oleic acid which has been reacted with 6 mols of ethylene oxide

Product B = iso-nonylphenol which has been reacted with 10 mols of ethylene oxide Product $C_1$ = formaldehyde condensate according to Example 1

Product $C_2$ = formaldehyde condensate according to Example 2.

The effectiveness of the levelling agent for the dyeing of polyester fibers with disperse dyestuffs is also determined by the so-called overboiling test, which is carried out as follows:

(a) Preliminary dyeing of the test material

A knitted fabric of texturised polyester filament is dyed, in a liquor ratio of 1:15, with a combination consisting of 0.3% of Disperse Blue 56 (C.I. No. 63285) and 0.1% of Disperse Yellow 5 (C.I. No. 12790), calculated as the pure dyestuff relative to the weight of fabric, without a special levelling agent and with the addition only of 1 g/l of monosodium phosphate and acetic acid at pH 4.5 and at 130° C. for 1 hour. The dyed fabric is rinsed and then after-treated with sodium hydroxide solution and hydrosulphite.

(b) Overboiling test

Equal parts by weight of fabric, and in particular first the washed, non-dyed knitted fabric of texturised polyester filament and, over that, the fabric dyed according to (a), are wound onto a specially perforated, cylindrical material carrier and are attached thereto with string. The sample thus prepared is treated, in a liquor ratio of 1:15, with 2 g/l of a levelling agent mixture which consists of 24 parts by weight of product A, 24 parts by weight of product B, 12 parts by weight of product $C_1$ and 40 parts by weight of $H_2O$ and which has been adjusted to pH 4.5 with monosodium phosphate/acetic acid, at 130° C. for 1 hour with a pulsating liquor under constant pump conditions. Examination of the two pieces of knitted fabric, wound onto the apparatus, shows a completely level dyeing on both.

The procedure followed is as under (5), 3 g/l of a levelling agent mixture consisting of 16 parts by weight of product A, 16 parts by weight of product B, 8 parts by weight of product $C_2$ and 60 parts by weight of $H_2O$ being used under (b).

In this case also, examination of the two pieces of knitted fabric, wound onto the apparatus, shows a completely level dyeing.

We claim:

1. A dispersing agent comprising
    (a) an addition product of an aliphatic, araliphatic or alkylaromatic alcohol, carboxylic acid or carboxylic acid amide with 12 to 22 C atoms and 3–8 mols of ethylene oxide,
    (b) an addition product of an aliphatic, araliphatic or alkylaromatic alcohol, carboxylic acid or carboxylic acid amide with 12 to 22 C atoms and 9 or more mols of ethylene oxide, and
    (c) a reaction product prepared by sulphonation or sulphomethylation and formaldehyde condensation of a compound of the formula

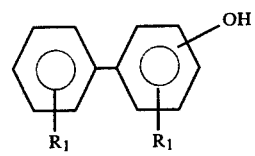

wherein
$R_1$ represents $C_{1-4}$-alkyl,
and, optionally, subsequent conversion of the resulting sulphonic acid into its salt.

* * * * *